(12) United States Patent
Glaros et al.

(10) Patent No.: US 11,162,128 B1
(45) Date of Patent: Nov. 2, 2021

(54) MASS SPECTROMETRY IONIZATION BASED-ASSAY FOR THE DETECTION OF ENZYME ACTIVITY AND/OR PRESENCE

(71) Applicant: U.S. Army Edgewood Chemical Biological Center, Apg, MD (US)

(72) Inventors: Trevor G Glaros, North East, MD (US); Elizabeth S Dhummakupt, Abingdon, MD (US); Phillip M. Mach, Edgewood, MD (US); Daniel O Carmany, Belcamp, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 364 days.

(21) Appl. No.: 15/976,120

(22) Filed: May 10, 2018

Related U.S. Application Data (60) Provisional application No. 62/509,956, filed on May 23, 2017.

(51) Int. Cl.
*C12Q 1/46* (2006.01)
*H01J 49/04* (2006.01)
*H01J 49/16* (2006.01)
*G01N 33/68* (2006.01)

(52) U.S. Cl.
CPC .......... *C12Q 1/46* (2013.01); *G01N 33/6848* (2013.01); *H01J 49/0445* (2013.01); *H01J 49/168* (2013.01); *C12Y 301/01007* (2013.01); *C12Y 301/01008* (2013.01); *G01N 2560/00* (2013.01)

(58) Field of Classification Search
CPC ...... C12Q 1/46; H01J 49/168; H01J 49/0445; G01N 33/6848; G01N 2560/00; C12Y 301/01007; C12Y 301/01008
See application file for complete search history.

(56) References Cited

U.S. PATENT DOCUMENTS

| | | | |
|---|---|---|---|
| 6,541,230 B1 * | 4/2003 | Gordon | C12N 11/00 435/175 |
| 2012/0040993 A1 * | 2/2012 | Youdim | C07C 211/38 514/252.11 |
| 2013/0181010 A1 * | 7/2013 | Ouyang | G01N 1/286 222/209 |
| 2016/0206635 A1 * | 7/2016 | Acey | C07F 9/242 |

OTHER PUBLICATIONS

Yan, X et al. Ambient ionization mass spectrometry measurement of aminotransferase activity. J. Am. Soc. Mass Spectrom. 2017. 28: 1175-1181. Published online Jan. 31, 2017. (Year: 2017).*
Wang, H et al. Paper spray for direct analysis of complex mixtures using mass spectrometry. Angew. Chem. Int. Ed. 2010. 49: 877-880. (Year: 2010).*
Bansal, V et al. Low operational stability of enzymes in dry organic solvents: changes in the active site might affect catalysis. Molecules. 2012. 17: 1870-1882. (Year: 2012).*
Damon, De et al. Direct biofluid analysis using hydrophobic paper spray mass spectrometry. Analytical Chemistry. 2016. 88: 1878-1884. Published Jan. 5, 2016. (Year: 2016).*

* cited by examiner

*Primary Examiner* — Renee Claytor
*Assistant Examiner* — Susan E. Fernandez
(74) *Attorney, Agent, or Firm* — Ulysses John Biffoni (57) ABSTRACT

An apparatus and method for detecting an analyte of interest using paper spray mass spectrometry includes a spray material; a sample on the spray material including an enzyme of interest; a solvent to hydrate the sample, promote enzymatic activity, and extract analytes of interest from the sample; a substrate specific to the enzyme of interest, wherein any of the spray material and the solvent includes the substrate; a voltage source to apply a voltage to the spray material to create charged droplets of a mixture containing the sample; and a mass spectrometer to perform spectrometry on the droplets to perform any of: identify the analytes of interest in the sample; and measure a level of inhibition in any enzymes contained in the sample.

9 Claims, 6 Drawing Sheets

102 Providing a spray material

↓

104 Applying a sample on the spray material

↓

106 Hydrating the sample with a solvent to promote enzymatic activity, and extract analytes of interest from the sample

↓

108 Applying a voltage to the spray material creating charged droplets of a mixture containing the sample

↓

110 Performing spectrometry on the droplets to identify the analytes of interest in the sample and to measure a level of inhibition in any enzymes contained in the sample

MASS SPECTROMETRY IONIZATION BASED-ASSAY FOR THE DETECTION OF ENZYME ACTIVITY AND/OR PRESENCE

CROSS REFERENCE TO RELATED APPLICATION

This application claims the benefit of U.S. Provisional Patent Application No. 62/509,956 filed on May 23, 2017, the contents of which, in its entirety, is herein incorporated by reference.

GOVERNMENT INTEREST

The embodiments herein may be manufactured, used, and/or licensed by or for the United States Government.

BACKGROUND

Technical Field

The embodiments herein generally relate to paper spray mass spectrometry (PS-MS), and more particularly to PS-MS for detection of biological molecules such as proteins which have an enzymatic property that may be leveraged to detect specific chemical signatures which are generated when the target protein cleaves a substrate into a product.

Description of the Related Art

Figure 1:
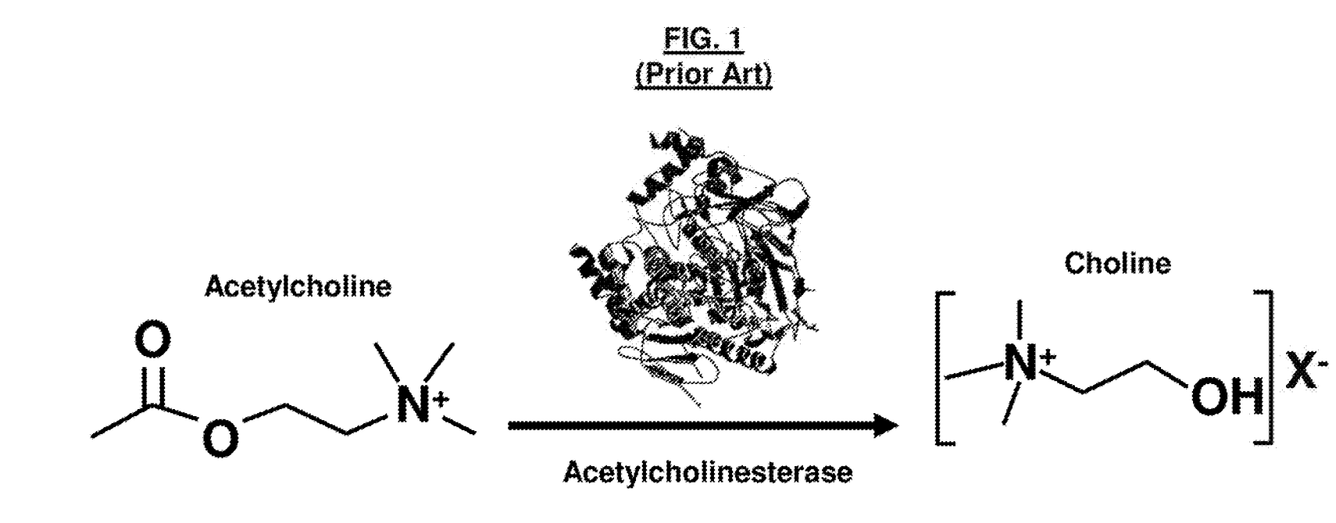
FIG. 1 is a schematic diagram illustrating an enzymatic reaction of acetylcholinesterase catalyzing the cleavage of acetylcholine into choline.

Acetylcholine (ACh) is the most widespread and best understood neurotransmitter. It is believed that an esterase is involved in its inactivation and removal from circulation. Research has previously identified cholinesterase (ChE) and FIG. 1 illustrates its ability to breakdown ACh. Today it is widely accepted that ChEs fall into two broad categories based upon substrate preferences; acetylcholinesterases (AChE) and butyrylcholinesterases (BChEs). The primary role of AChE is to catalyze the rapid hydrolysis of ACh in the cholinergic synapses within the center nervous system, the peripheral nervous system, and at neuromuscular junctions. When this function is impeded by potent inhibitors such as organophosphate (OP) pesticides it will lead to nerve signal transmission dysfunction. Like many proteins, AChE exists in several different isoforms which are widely distributed throughout the body; however, each isoform has identical catalytic properties. Of these isoforms, the erythrocytic isoform (AChE-E) is the most accessible for assay developed due to its location on red blood cells. BChE is most abundant in the liver but is also readily found in the blood and is commonly known as plasma cholinesterase. Unlike AChE, the biological role of BChE is not fully understood. Although it hydrolyzes ChE, it is thought to function primarily as a scavenging enzyme for detoxification. It has also been implicated in a number of neurodegenerative and cardiovascular diseases.

The primary reason for measuring ChE is to diagnosis human exposure to pesticides which act as ChE-inhibitors; most notably organophosphates (OPs) and carbamates. To date there are more than 200 different OPs and carbamates which have been formulated into numerous products. Given the widespread usage of these poisons and the relatively poor health surveillance it is generally impossible to estimate the actual global health impact. Nonetheless, more than 3 million self-poisonings with organophosphate pesticides occur globally each year resulting in roughly 200,000 deaths. Signs and symptoms from poisoning may vary greatly depending upon the compound, the dose, and length of exposure. Acute life-threatening exposures typically impact the respiratory centers within the brainstem and frequently result in death. Intermediate syndromes may also develop especially to lower levels of exposure and is characterized by muscle weakness especially in respiratory, neck, and limb muscle groups. These symptoms may occur hours, days, or weeks post exposure. Diagnosis to ChE-inhibiting compounds may be difficult especially since the compounds may have varying degrees of affinity for AChE and BChE. Additionally, some of the OPs, especially the chemical warfare agents (CWAs), may bind irreversibly. For acute exposure diagnosis, ChE test data is typically only ordered in instances where the poison is known or suspected to be a ChE-inhibitor. On the other hand, ChE inhibition is quite useful for medical surveillance applications especially for employees who are at higher risks of exposure in the workplace.

Although several different ChE inhibition assays have been developed since the 1940's, the delta-pH assay and the Ellman assay are the most commonly used. Both of these assays are based upon the products which are produced when AChE cleaves its target substrate. Additionally, these assays are generally only able to measure either AChE or BChE. In order to establish the level of inhibition of both enzymes, two separate assays must be run typically with the inclusion of a BChE specific inhibitor while measuring AChE activity. The delta-pH technique is the mostly widely used since it is currently the routine test that is used to monitor more than 25,000 people annually at the U.S. Army Center for Health Promotion and Preventive Medicine (USACHPPM). For this test, acetylcholine is the substrate of choice which, when cleaved, produces acetic acid and choline. The production of acetic acid is used to monitor the pH change over time. Even though this technique is streamlined it still takes approximately 17 minutes to perform the assay which severely limits the throughput and feasibility of implementation for commercial laboratories. The more sensitive Ellman assay is a color-based system that uses acetylthiocholine as the substrate which when cleaved, yields both acetate and thiocholine. Thiocholine is used to react with 5,5'-dithiobis-2-nitrobenzoic acid to produce a yellow color which is measured with a spectrophotometer. The Ellman assay has been commercialized into a field-testing system by EQM Research and is commonly known as the Test-mate™ assay. This assay is less sensitive than the laboratory-based equivalent, but only takes four minutes to complete using only 10 µL of blood.

Generally, all the assays used to detect AChE and BChE inhibition leverage technology and approaches that have remained unchanged for more than 50 years. Even though both techniques have been perfected, the assay, especially from lab-to-lab, has a significant source of variability (>20%) and requires fresh liquid blood. Therefore, even today it is important that a 'baseline' activity is established for monitored personnel within the same lab using the exact same process or standard operating procedure. Although efforts have been made to standardize the process and to develop algorithms that may cross compare the different approaches, with the exception of an acute exposure event where there is a massive BChE and AChE inhibition, it remains difficult to confidently diagnosis low-level exposures. Additionally, the conventional techniques typically only address the levels of enzyme inhibition and fail to identify the toxicant.

SUMMARY

In view of the foregoing, an embodiment herein provides an apparatus for detecting an analyte of interest using paper spray mass spectrometry, the apparatus comprising a spray material; a sample comprising AChE and BChE enzymes; a solvent to hydrate the sample, promote enzymatic cleavage, and extract analytes of interest; an enzyme substrate specific to any of AChE and BChE and comprising 1,1-dimethyl-4-acetylthiomethylpiperidinium iodide (MATP+) and butyrylthiocholine, wherein any of the spray material and the solvent comprises the enzyme substrate; a power supply to apply a voltage to the spray material creating charged droplets of the analytes of interest contained within the sample; and a mass spectrometer to identify the analytes of interest in the sample and to determine a presence of the enzymes contained in the sample.

The spray material may comprise any of a porous and solid surface. The solvent may comprise any of a single and multi-solvent to hydrate the sample on the spray material and permit an enzymatic reaction of the hydrated sample to occur with the spray material; promote an enzymatic activity of the enzymes to cleave the spray material into its detected product; terminate an enzymatic reaction after a predetermined period of time; extract the analytes of interest from the sample; and promote ionization of the analyte from the sample upon application of the voltage to the spray material. The sample may comprise any of blood, urine, interstitial fluid, plasma, and serum. The mass spectrometer is to directly identify the analyte of interest. The solvent may comprise a solvent spray. The solvent may comprise any of tridecane, cyclohexane, hexane, n-octane, iso-octane, ethyl ether, heptane, tetrachloroethane, hexadecane, toluene, dodecane, carbon tetrachloride, and benzene. The voltage may be approximately 2-5 kV.

Another embodiment provides an apparatus for detecting an analyte of interest using paper spray mass spectrometry, the apparatus comprising a spray material; a sample on the spray material comprising an enzyme of interest; a solvent to hydrate the sample, promote enzymatic activity, and extract analytes of interest from the sample; a substrate specific to the enzyme of interest, wherein any of the spray material and the solvent comprises the substrate; a voltage source to apply a voltage to the spray material to create charged droplets of a mixture containing the sample; and a mass spectrometer to perform spectrometry on the droplets to perform any of: identify the analytes of interest in the sample; and measure a level of inhibition in any enzymes contained in the sample.

The spray material may comprise any of paper, glass, and polyethelene. The solvent may comprise any of a single and multi-solvent to hydrate the sample on the spray material and permit an enzymatic reaction of the hydrated sample to occur with the spray material; promote an enzymatic activity of the enzyme of interest to cleave the spray material into its detected product; terminate an enzymatic reaction after a predetermined period of time; extract the analytes of interest from the sample; and promote ionization of the analyte from the sample upon application of the voltage to the spray material. The spray material may comprise paper. The sample may comprise any of a biological material, a chemical, and an environmental material.

Another embodiment provides a method for detecting an analyte of interest using paper spray mass spectrometry, the method comprising providing a spray material; applying a sample on the spray material, wherein the sample comprises an enzyme of interest; hydrating the sample with a solvent to promote enzymatic activity, and extracting analytes of interest from the sample; applying a voltage to the spray material creating charged droplets of a mixture containing the sample; and performing spectrometry on the droplets to identify the analytes of interest in the sample and to measure a level of inhibition in any enzymes contained in the sample.

The solvent may comprise any of a single and multi-solvent to hydrate the sample on the spray material and permit an enzymatic reaction of the hydrated sample to occur with the spray material; promote an enzymatic activity of the enzyme of interest to cleave the spray material into its detected product; terminate an enzymatic reaction after a predetermined period of time; extract the analytes of interest from the sample; and promote ionization of the analyte from the sample upon application of the voltage to the spray material. The predetermined period of time is approximately one minute. The enzyme of interest may comprise AChE and BChE. As the ionization proceeds, a rate of ACh catalysis is captured as an amount of choline detected, and wherein the mass spectrometer is to use the amount of choline detected to calculate a level of inhibition in the AChe. The spectrometry directly identifies a toxicant in the sample. Any of the spray material and the solvent may comprise an enzyme substrate specific to the enzyme of interest.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a technique utilizing PS-MS, which is a new ionization technique that has been demonstrated to successfully detect a wide range of chemicals, including CWA simulants and hydrolysis products directly from whole blood and urine. This approach requires no sample preparation and is extremely rapid (~1 min) while retaining high levels of sensitivity and selectivity. A diagnostic assay is given as an example of an enzymatic assay that may be used to establish acetylcholinesterase and butyrylcholinesterase inhibition, while simultaneously detecting the CWA and its metabolite. Unlike the conventional solutions, the embodiments herein offer a faster determination of enzyme activity/inhibition, while also identifying the toxicant. Information from this assay will better inform the therapeutic approach including the administration of the appropriate countermeasure. Referring now to the drawings, and more particularly to FIGS. 1 through 5, there are shown preferred embodiments.

The chemical reactions that take place via enzymes are rapid and specific in nature. Each enzyme performs a specific reaction on a specific molecular target or targets, referred to as substrates. This reaction a substrate undergoes via an enzyme results in a changed molecule referred as a product. Chemical detectors have the ability to detect the substrate, enzyme, and product. Furthermore, monitoring the quantities of each over time, will result in observing the conversion of the substrate into the product molecular species. This ongoing reaction is important for development and usage of assays to detect the presence of a given enzyme, substrate, or product or determine the inhibition of such a reaction. Almost all metabolic processes require an enzymatic reaction to convert molecular substrates at physiological relevant rates, and one such reaction is the acetylcholinesterase enzymatic hydrolase. The AChE reaction is the chemical breakdown of acetylcholine, and related choline esters (natural and synthetic), into choline and acetate-type molecules. Acetylcholine serves as a neurotransmitter and is required for proper operation of nervous system. The paper spray technique offers an ability to detect, not only the AChE enzymatic reaction, but all reactions with a substrate and product that is detectable by a chemical detector. The paper spray technique utilizes mass spectrometry, one such chemical detection, by detecting the quantities of acetylcholine and choline. Utilizing synthetic substrates specifically for the AChE enzyme, a known quantity may be utilized to standardize the reaction and provide accurate feedback relating to the efficiency of the enzymatic reaction, and if it is inhibited. Furthermore, chemical detectors like mass spectrometers utilizing paper spray technique have the ability to detect the chemical inhibiting the enzymatic reaction, allowing for another dimension of data obtainable.

The embodiments herein utilize a paper-based ionization technique, that when paired with a mass spectrometer, allows for the detection of small molecules directly from complex matrices such as whole blood, urine, and various environmental samples. The PS-MS technique utilized by the embodiments herein, requires no sample preparation, uses extremely low levels of solvent, and may be performed in as little as one minute. Although PS-MS is relatively new, it has been shown to be effective in many diverse applications including the detection of pesticides, fungicides, illicit drugs, explosives, bacterial identification, toxin identification, and direct aerosol capture and identification.

Figure 2A:
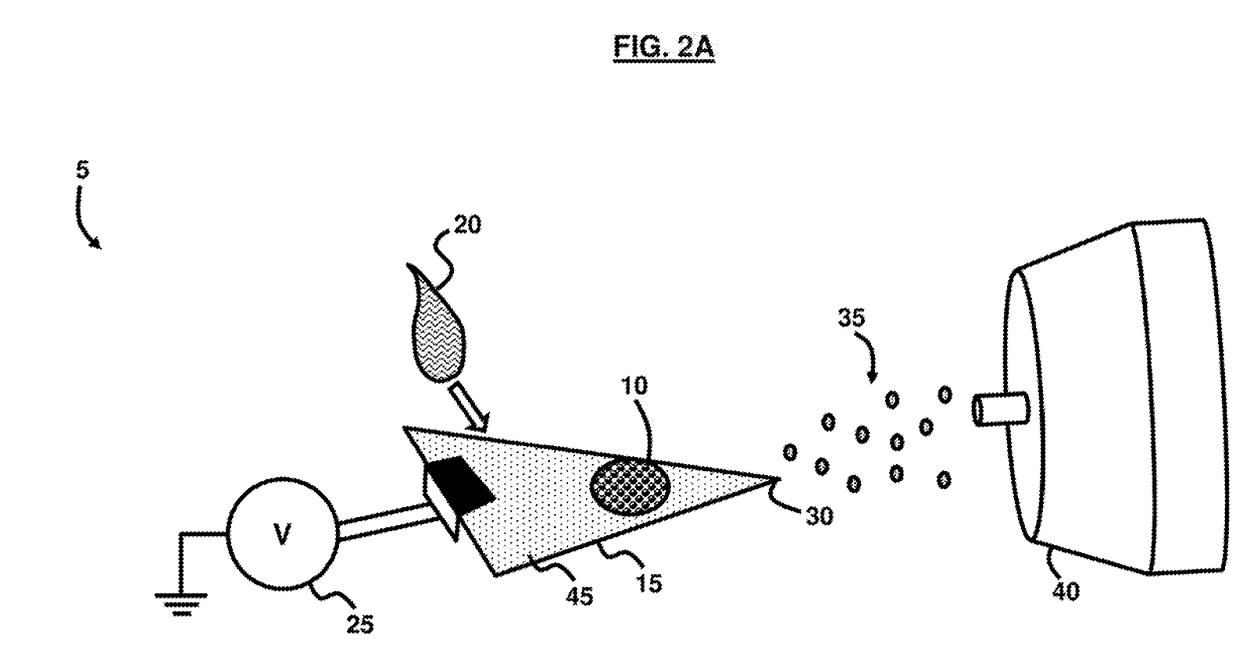
FIG. 2A is a schematic diagram illustrating an apparatus for performing an assay procedure, according to a first example.
Figure 2B:
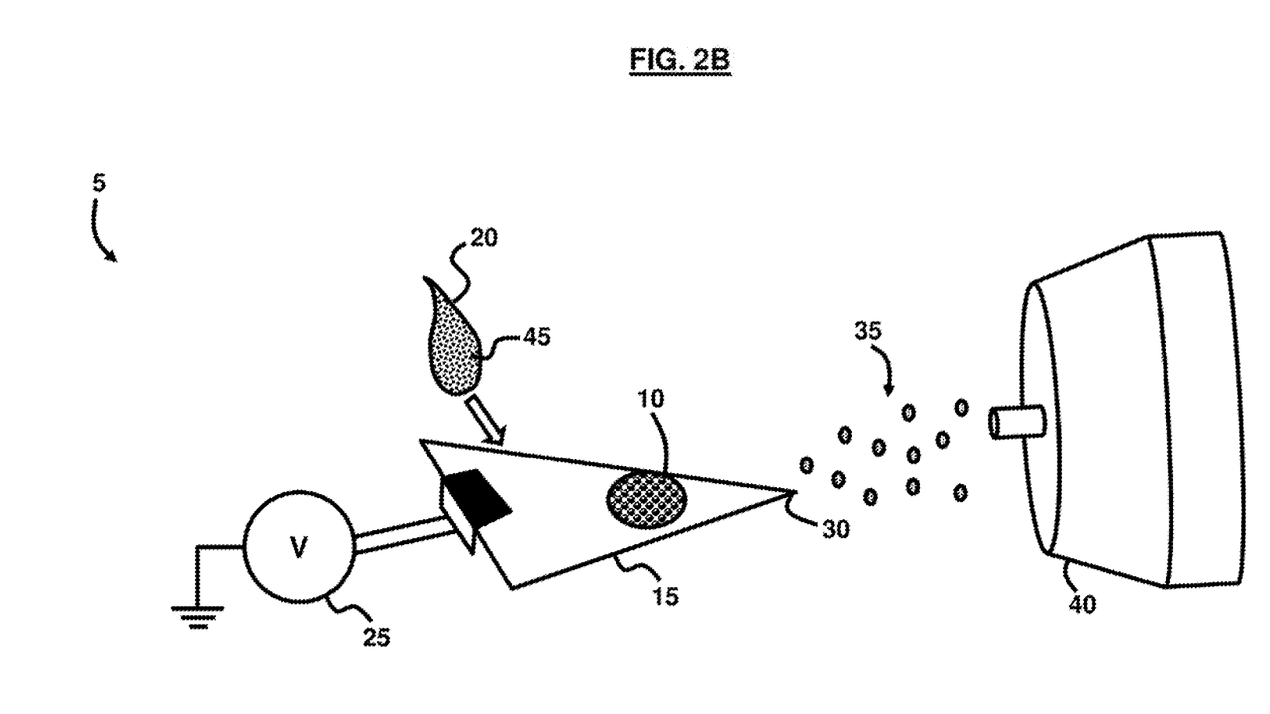
FIG. 2B is a schematic diagram illustrating an apparatus for performing an assay procedure, according to a second example.

FIGS. 2A and 2B illustrate examples of an apparatus 5 for conducting an assay utilizing a paper spray ionization process. To conduct this assay, approximately 10 µL of sample 10 such as blood, urine, sweat, saliva, interstitial fluid, plasma, serum, or environmental samples (also referred to herein as 'sample' for ease of description and not for limitation of any specific type of sample 10 used in accordance with the embodiments herein) is spotted onto the spray material 15, which may comprise paper, glass, polyethelene, among other porous or non-porous materials. The sample 10 is then hydrated with a solvent 20 that is both compatible for enzymatic activity, extraction of the analyte of interest, and 'electrospray-like' ionization. This is an example of a single solvent system. Multi-solvent systems may be used if one solvent isn't compatible for all the steps described above. The solvent 20 is applied for less than five seconds followed by a rest period of approximately less than one minute. As shown in FIG. 2A, the spray material 15 may comprise an enzyme substrate 45, which includes molecules upon which an enzyme acts. Examples of the substrate 45 are described in further detail below. In FIG. 2B, the solvent 20 may comprise the enzyme substrate 45.

A voltage source 25 applies a voltage to the spray material 15. In an example, the voltage may be approximately 2-5 kV, and in one example approximately 3.5 kV. The voltage initiates the 'electrospray-like' ionization from the tip 30 of the spray material 15 immediately creating charged droplets 35, which then enter the mass spectrometer 40 for analysis for a period of one to two minutes. As an example, an application for the PS-MS technique described in accordance with the embodiments herein, is a new single AChE and BChE inhibition assay that may be performed in as little as one minute from a single spot of sample 10 while simultaneously establishing both the level of inhibition and identifying the toxicant within the sample 10.

Acetylcholinesterase and butyrylcholinesterase are capable of catalyzing the same reaction; however, since their discovery some unique substrates and specific inhibitors have been identified and may be used as the substrate 45 in accordance with the embodiments herein. For example, 1,1-dimethyl-4-acetylthiomethylpiperidinium iodide (MATP+) may be used as the substrate 45, which is specific for only AChE and not BChE. Additionally, butyrylthiocholine (BuTC) has been shown to be specific for only BChE. Therefore, for the assay, the solvent 20 may be used for a mix of these substrates 45, and is used to hydrate the sample 10 to initiate enzymatic activity. Alternatively, the spray material 15 may be pretreated with the substrate 45 to initiate cleavage when the sample 10 is applied. Since the technique provided by the embodiments herein may delineate the difference in products by mass and does not leverage the generic reactivity of the products for a secondary reaction, the assay is able to establish the activity levels of both enzymes simultaneously.

In an example, the AChE/BChE assay described herein may be developed around a dried blood spot (DBS) sample 10 instead of a 'wet' blood spot, which is preferable for several reasons described below. However, in other examples a 'wet' blood spot may also be used. The enzyme activity is significantly preserved in dried blood spots that are stored for several weeks outside of a cold chain. First, analytes and even enzymatic activity within DBS may be much more stable and hence have a longer shelf life compared to whole blood stored as a liquid. Additionally, DBS are not considered as a biohazard, so they may easily be shipped from location to location without any biohazard logistics or requirements. Finally, since many of the carbamates only result in a transient inhibition of the ChEs, storing the material dry should prevent the reactivation of the ChEs which commonly results in false negatives. Since the amount of enzymes present within a given volume of blood is highly dependent upon the number of red blood cells, the embodiments herein also establish the amount of heme present. This factor may be used to normalize activity so that it may be expressed as units per gram of hemoglobin (U/g Hgb).

The solvent optimization for the assay is an extremely important consideration. Typically, PS-MS is performed using a single solvent that is both capable of extracting the analytes of interest from the DBS and also effective in producing a spray from the paper tip. For biological matrices such as blood, 95:5 methanol:water supplemented with 0.01% formic acid is commonly used. However, for this assay that solvent will not be suitable as the sole solvent because AChE and BChE are not catalytically active in methanol concentrations greater than 10%. Additionally, both enzymes are pH sensitive, so the addition of formic acid would likely halt the reaction.

Figure 3:
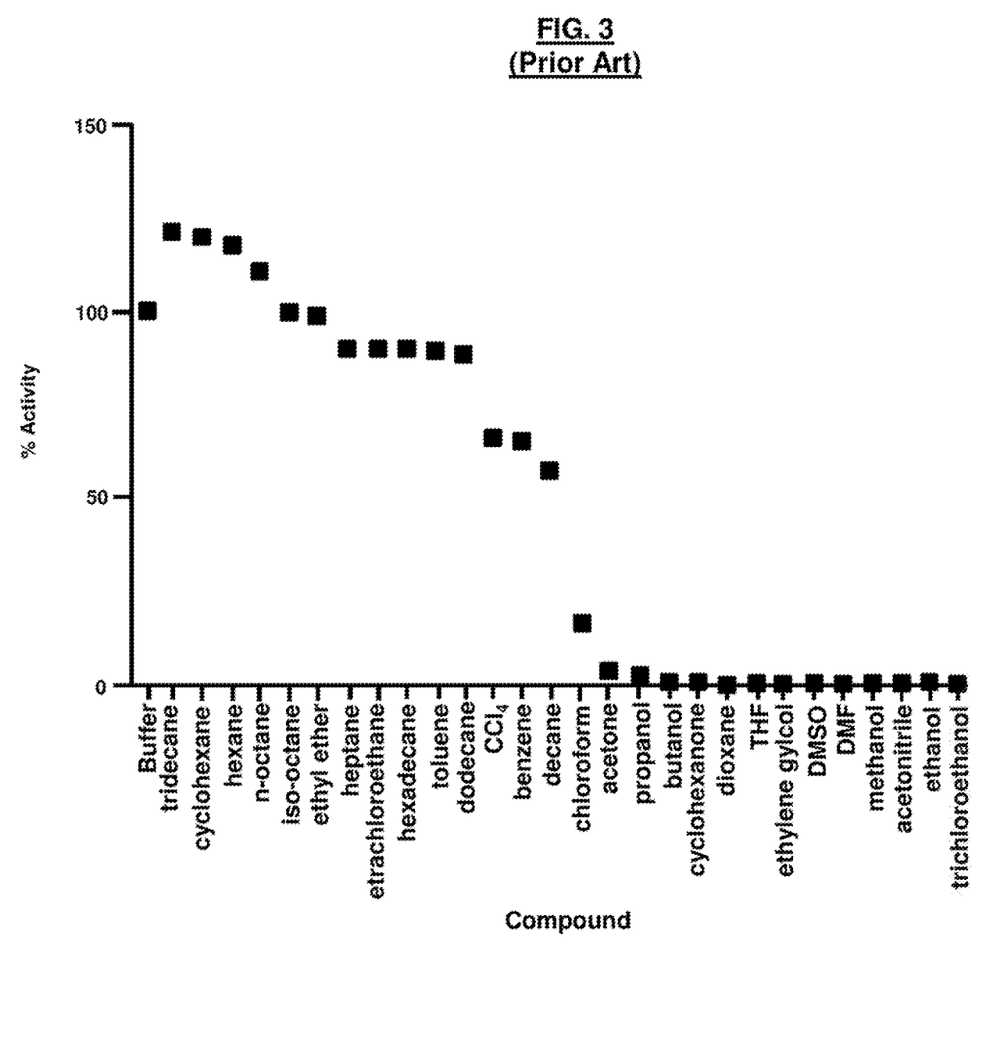
FIG. 3 is a graph illustrating potential solvent systems which may preserve the percent activity of the enzyme acetylcholinesterase.

The industry has shown that enzymatic activity is preserved in solvents that have been shown to produce good 'ionization sprays' as shown in FIG. 3, as described in Mionetto, N., et al., "Acetylcholinesterase in organic solvents for the detection of pesticides: Biosensor application," Biosensors and Bioelectronics, Vol. 9, Issue 6, pp. 463-470, December 1994, the complete disclosure of which, in its entirety, is herein incorporated by reference. Some example solvents include tridecane, cyclohexane, hexane, n-octane, iso-octane, ethyl ether, heptane, tetrachloroethane, hexadecane, toluene, dodecane, carbon tetrachloride, and benzene, among others. This approach may be preferable for capturing a continuous read of enzymatic activity over time. Additionally, this approach would make establishing the rate easier without too much emphasis on the start and stop time of the assay.

The embodiments herein may utilize a multi-solvent system. First, a hydration solvent or buffer is formulated that contains the optimal conditions (e.g., approximately 22-30° C. and ambient air) for the enzyme/substrate 45 reaction. Examples of hydration solvents or buffers that may be used include toluene/methanol, hexanes, hexane/toluene, pentane, and phosphate-buffered saline. This solvent 20 is applied to the sample 10 and serves two purposes: to hydrate the sample 10 and to allow for the enzymatic reaction to take place. Then, a second solvent system is used to halt the reaction, assist with the extraction of the substrates 45 and products, and to promote ionization required for mass spectrometer analysis. Examples of solvents used in the second solvent system include methanol/water, chloroform/methanol, acetonitrile/methanol, acetonitrile/water, and acidic solutions. Since the time between solvent applications is tightly controlled a delta time may be determined and used to establish a catalytic rate which is essential for inhibition calculations. In other words, the time from first solvent addition, starting the reaction for AChE/BChE activity, to the application of the second solvent system, which ends the process on the spray material 15, the total number of ions may be counted per second, allowing for a deduction regarding the quantities of active molecules. Since the toxicant is also present within the sample 10, the assay will be able to qualitatively assess the toxicant's presence without any additional considerations. Quantitation may be determined by the addition of an internal standard (ISTD).

Figure 4:
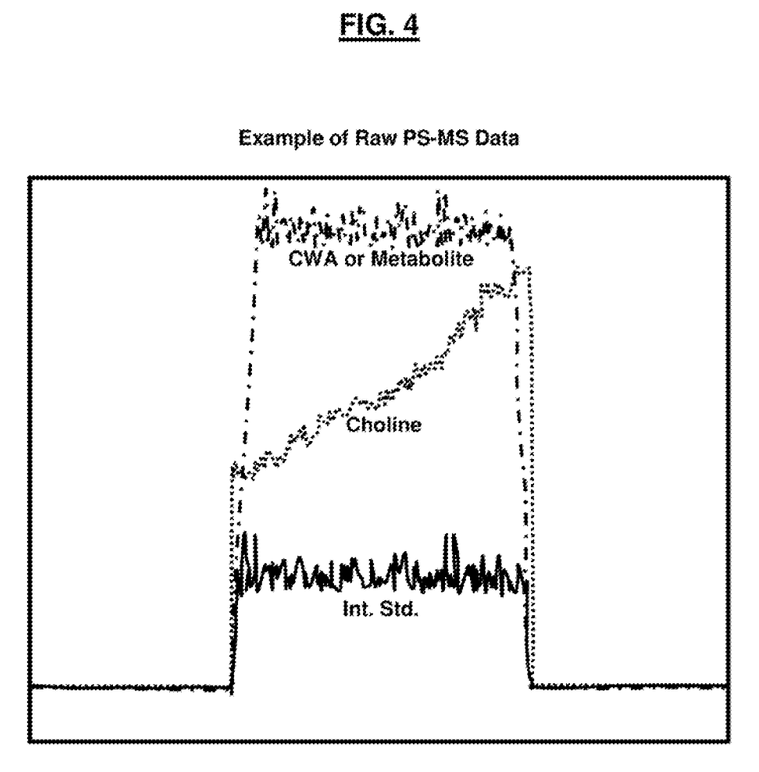
FIG. 4 is a graph illustrating an example of raw data generated using a single solvent system.

A series of ISTDs are incorporated so accurate quantitative assessments for each measurement component may be made. ISTDs are commonly incorporated into mass spectrometry based assays which are used as points of reference. These standards compensate for assay conditions that are not easily controlled such as temperature and ionization spray stability. ISTDs will be required each facet of the assay including the enzymatic products (e.g., thiocholine), for heme, and for potential toxicants. By leveraging these ISTDs, the embodiments herein are able to quantitatively establish the enzyme kinetics which will be required for establishing percentage of inhibition. With respect to the ISTDs used in accordance with the embodiments herein, specific quantities of non-anthropogenic substrates 45 are added at known quantities, by which AChE will cleave at known rates. This ISTD will be similar across all samples, with reproducible results depending on the state of the AChE/BChE enzyme. Depending upon the optimized solvent system the kinetics may be established and normalized in two distinct ways. First, if a two-solvent system is used, rate measurements will be based upon a single measurement and a fixed time. If a single solvent system is used, as indicated in FIG. 4, it may be possible to establish the rate based upon multiple readings over the one-minute data acquisition window. FIG. 4 shows the amount and quality of data obtained. The test allows for the detection of the actual AChE/BChE inhibitor (e.g., the CWA), the rate of inhibition, and the ability to quantify the rate of reaction with the ISTD. FIG. 4 depicts an example of how the data would look if the spray solvent 20 was compatible with the enzymatic reaction; i.e., does not inhibit the cleavage of the substrate 45 by denaturing the AChE or BChE.

Figure 5:
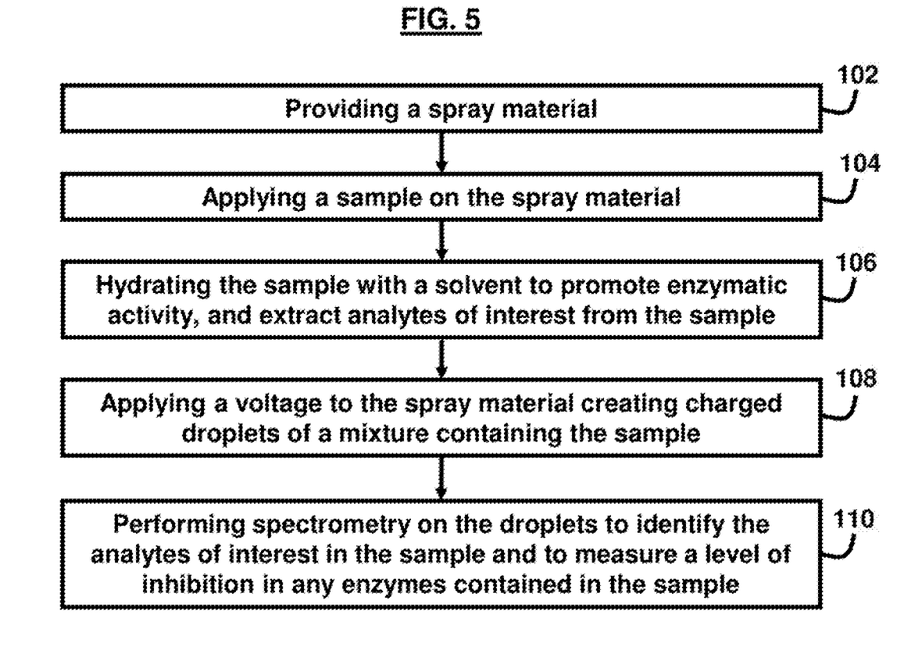
FIG. 5 is a flow diagram illustrating a method for detecting an analyte of interest using paper spray mass spectrometry.

FIG. 5, with reference to FIGS. 1 through 4, is a flow diagram of a method for detecting an analyte of interest using paper spray mass spectrometry, the method comprising providing (102) a spray material 15; applying (104) a sample 10 on the spray material 15, wherein the sample 10 comprises an enzyme of interest; hydrating (106) the sample 10 with a solvent 20 to promote enzymatic activity, and extract analytes of interest from the sample 10; applying (108) a voltage to the spray material 15 creating charged droplets 35 of a mixture containing the sample 10; and performing (110) spectrometry on the droplets 35 to identify the analytes of interest in the sample 10 and to measure a level of inhibition in any enzymes contained in the sample 10.

The solvent 20 may comprise any of a single and multi-solvent 20 to hydrate the sample 10 on the spray material 15 and permit an enzymatic reaction of the hydrated sample 10 to occur with the spray material 15; promote an enzymatic activity of the enzyme of interest to cleave the spray material 15 into its detected product; terminate an enzymatic reaction after a predetermined period of time; extract the analytes of interest from the sample 10; and promote ionization of the analyte from the sample 10 upon application of the voltage to the spray material 15. The predetermined period of time is approximately one minute. The enzyme of interest may comprise AChE and BChE. As the ionization proceeds, a rate of ACh catalysis is captured as an amount of choline detected, and wherein the mass spectrometer is to use the amount of choline detected to calculate a level of inhibition in the AChe. The spectrometry directly identifies a toxicant in the sample 10. Any of the spray material 15 and the solvent 20 may comprise an enzyme substrate specific to the enzyme of interest.

Several features are provided by the embodiments herein including: rapid (approximately one minute per run) testing, comprehensive testing by establishing AChE and BChE inhibition as well as toxicant identification, inexpensive testing (approximately <$4 per run) utilizing commercial off-the-shelf PS-MS technology, a demonstrably proven technique for the detection of explosives, illicit drugs, and CWAs (clinical and aerosols), and provides an informed therapy test by identifying toxicants.

While the embodiments described herein refer to an AChE/BChE enzymatic assay to be analyzed by paper spray mass spectrometry, this is just one example of an enzymatic assay that may be performed on the spray material 15. In this regard, various enzymatic assays may take place on the spray material 15; both on the surface or within the spray material 15. This may include a variety of non-paper materials 15 both modified and unmodified. For example, surfaces of the spray material 15 may be modified with a variety of chemistries that make the surfaces more hydrophilic or hydrophobic. Additionally, the surface of the spray material 15 may be modified in a way to facilitate the reaction. An example is pre-treating the surface of the spray material 15 with the enzymatic substrates 45 or with various co-factors to better facilitate the reaction.

Furthermore, although the descriptions above may refer to blood-based biological assays, the embodiments herein may utilize non-biofluid material such as environmental samples for the sample 10. This may include soil, water, and various surfaces (sampled using wipes or with the spray material 15). An example of an enzymatic environmental application could be for the detection of many of the biothreat toxins (Ricin, Abrin, Bot Tox). All of these toxins work by performing a variety of different types of enzymatic reactions with in the host thus resulting in toxicity. However, by using intelligently designed probes it is possible to get these toxins to cleave the probe substrate 45 on the paper surface (or within) liberating a small molecule specific marker that may be easily read by PS-MS. This would allow for the detection of the toxin by leveraging its activity.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. An apparatus for detecting an analyte of interest using paper spray mass spectrometry, the apparatus comprising:
    a spray material;
    a sample that may contain one or more analytes of interest and includes acetylcholinesterase (AChE) and butyrylcholinesterase (BChE) enzymes, said sample applied to and disposed on said spray material;
    a solvent to hydrate the sample, promote enzymatic cleavage, and extract the analytes of interest contained within the sample, said solvent applied to and disposed on said spray material;
    an enzyme substrate specific to AChE and BChE and comprising 1,1-dimethyl-4-acetylthiomethylpiperidinium iodide (MATP+) and butyrylthiocholine, wherein any of the spray material and the solvent includes the enzyme substrate;
    a power supply to apply a voltage to the spray material creating charged droplets of the analytes of interest contained within the sample; and
    a mass spectrometer to identify the analytes of interest contained within the sample and to determine a presence of the enzymes contained in the sample.

2. The apparatus of claim 1, wherein the spray material comprises any of a porous and solid surface.

3. The apparatus of claim 1, wherein the solvent comprises a single solvent or a multi-solvent to:
    hydrate the sample on the spray material and permit an enzymatic reaction of the hydrated sample to occur on the spray material;
    promote an enzymatic activity of the enzymes to cleave the enzyme substrate into its detected product comprising the analytes of interest;
    terminate an enzymatic reaction after a predetermined period of time;
    extract the analytes of interest from the sample; and
    promote ionization of the analytes of interest from the sample upon application of the voltage to the spray material.

4. The apparatus of claim 1, wherein the sample comprises any of blood, urine, interstitial fluid, plasma, and serum.

5. The apparatus of claim 1, wherein the mass spectrometer directly identifies the one or more analytes of interest.

6. The apparatus of claim 1, wherein the solvent comprises a solvent spray.

7. The apparatus of claim 1, wherein the solvent comprises any of tridecane, cyclohexane, hexane, n-octane, iso-octane, ethyl ether, heptane, tetrachloroethane, hexadecane, toluene, dodecane, carbon tetrachloride, benzene, pentane, methanol, water, chloroform, acetonitrile, and mixtures thereof.

8. The apparatus of claim 1, wherein the voltage is approximately 2-5 kV.

9. The apparatus of claim 1, wherein said spray material comprises any of paper, glass, and polyethylene.

* * * * *